United States Patent
Kittock et al.

(10) Patent No.: US 7,128,874 B2
(45) Date of Patent: Oct. 31, 2006

(54) METHOD AND SYSTEM FOR PICKING AND PLACING VESSELS

(75) Inventors: Mark J. Kittock, Eden Prairie, MN (US); Brian D. Wilson, Chaska, MN (US); Humayun Qureshi, Eden Prairie, MN (US); Armer J. Willenbring, Minnetonka, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 960 days.

(21) Appl. No.: 09/771,471

(22) Filed: Jan. 26, 2001

(65) Prior Publication Data

US 2002/0102736 A1    Aug. 1, 2002

(51) Int. Cl.
   *B32B 5/02*    (2006.01)
(52) U.S. Cl. .................. 422/63; 294/27.1; 294/106; 294/116; 294/85; 436/43; 81/3.31
(58) Field of Classification Search ............... 436/180, 436/807, 808, 809, 810, 43; 422/63, 65, 422/99, 100, 102, 104; 294/2, 25, 65.5, 902, 294/27.1, 85, 106, 116; 81/3.31
See application file for complete search history.

(56) References Cited

U.S. PATENT DOCUMENTS

| | | | | |
|---|---|---|---|---|
| 2,899,232 A | 8/1959 | Walter, Jr. | ................. | 294/65 |
| 3,554,594 A | 1/1971 | Thoma | ........................ | 294/90 |
| 4,257,639 A | 3/1981 | Stock | .......................... | 294/83 |
| 4,492,400 A * | 1/1985 | Yuda | ............................ | 294/88 |
| 4,611,846 A | 9/1986 | Feiber et al. | .................. | 294/88 |
| 4,705,311 A | 11/1987 | Ragard | .......................... | 294/2 |
| 4,723,503 A * | 2/1988 | Yuda | .......................... | 116/204 |
| 4,810,018 A | 3/1989 | van de Ven et al. | .......... | 294/88 |
| 4,892,344 A | 1/1990 | Takada et al. | ................. | 294/88 |
| 5,236,239 A | 8/1993 | Govang et al. | ............. | 294/86.4 |
| 5,295,723 A | 3/1994 | Kronseder | .................... | 293/88 |
| 5,775,755 A | 7/1998 | Covert et al. | .................. | 294/88 |
| 5,948,360 A | 9/1999 | Rao et al. | ...................... | 422/65 |
| 6,520,315 B1 * | 2/2003 | Sugarman et al. | .......... | 198/379 |
| 6,544,799 B1 * | 4/2003 | Lewis et al. | ................. | 436/180 |
| 6,652,015 B1 * | 11/2003 | Carney et al. | ............. | 294/86.4 |

FOREIGN PATENT DOCUMENTS

JP          4046789          5/1992

* cited by examiner

*Primary Examiner*—Jill Warden
*Assistant Examiner*—Jyoti Nagpaul
(74) *Attorney, Agent, or Firm*—Hogan & Hartson LLP

(57) ABSTRACT

A method and system for picking and placing vessels are provided. The system includes a gripper assembly mounted on a positioning mechanism. The gripper assembly includes a cylinder, a plurality of flexible gripping members extending from the cylinder in a spaced-apart relationship for receiving therebetween a vessel and holding it by friction, a piston slideably inserted inside the cylinder, and a plunger connected to and movable with the piston and extending between the gripping members for engaging the vessel. The method includes the steps of positioning the gripper assembly, picking up and transferring a vessel, and placing, seating and releasing the vessel. The contents of the vessel may also be mixed simultaneously during the transferring of the vessel.

27 Claims, 4 Drawing Sheets

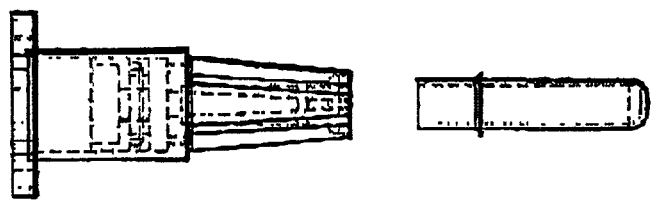
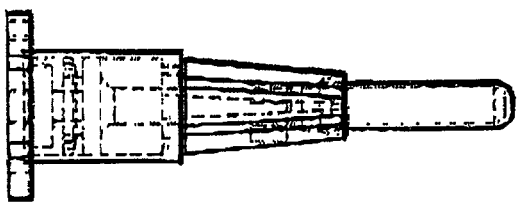
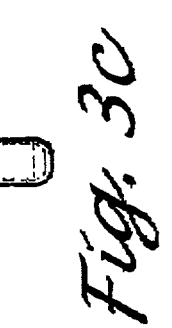
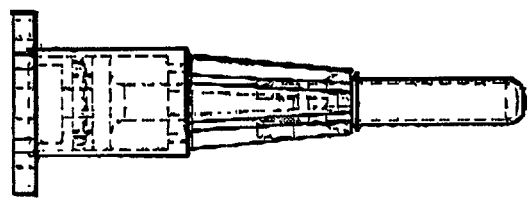
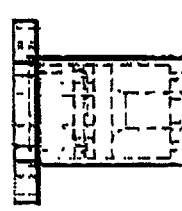
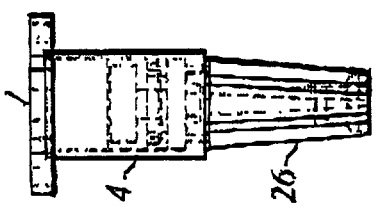

METHOD AND SYSTEM FOR PICKING AND PLACING VESSELS

BACKGROUND OF THE INVENTION

1. Area of the Art

The present invention relates generally to vessels handling methods and systems used in conjunction with automated chemical analyzer instruments and, more specifically, to methods and systems for picking and placing vessels used in conjunction with automated chemical analyzer instruments.

2. Description of the Prior Art

Automated chemical analyzers, particularly immunodiagnostic instruments, are widely used in clinical chemistry sampling and analyzing applications. The instruments often involve the handling of vessels for performing various assays. The basic functions of handling vessels typically involve picking, transferring, and placing the vessels, and mixing their contents for processing and analyzing by an automated chemical analyzer. During the transfer process, the vessel and its contents must be moved smoothly. Jarring the vessel may cause the contents to either splash out of the vessel, or if splashing does occur, droplets may stick to the walls of the vessel at the top. Either of these events may affect accuracy of the results.

The following references are found to be pertinent to the field of the present invention:

U.S. Pat. No. 2,899,232, issued to Walter, Jr. on Aug. 11, 1959, disclosed a bottle chuck adapted for handling bottles. The bottle chuck has a series of threadedly connected cylindrical pieces and jaws for engaging bottle necks and a spring-loaded piston rod for engaging the bottle caps.

U.S. Pat. No. 3,554,594, issued to Thoma on Jan. 12, 1971, disclosed a pneumatically-operated gripper for bottles. The gripper has a plurality of fingers bound by a sleeve, such that the upward movement of the sleeve will engage the fingers and a downward movement of the sleeve will release the fingers.

U.S. Pat. No. 4,257,639, issued to Stock on Mar. 24, 1981, disclosed an ejector device for ejecting a store from an aircraft store rack. The device includes lug-retaining fingers and a collar for holding the fingers in engagement with a lug mounted on the store. Removing the collar causes the fingers to disengage from the lug for releasing the store.

U.S. Pat. No. 4,611,846, issued to Feiber et al. on Sep. 16, 1986, disclosed a gripper head for attachment to a vertical axis of a robot or a pick-and-place machine for picking up components and placing them on a workpiece. The gripper head has two opposite piston and cylinder units, and two opposite jaws, each driven by a respective piston and cylinder unit to move in a transverse direction for gripping the components.

U.S. Pat. No. 4,705,311, issued to Ragard on Nov. 10, 1981, disclosed a component pick and placement spindle assembly for surface mounting and insertion of electrical components. The assembly includes a mechanism for squaring the component to an orthogonal coordinate system and also an orienting means comprising a direct drive rotary motor operatively associated with a tool assembly having component engaging fingers.

U.S. Pat. No. 4,810,018, issued to van de Ven et al. on Mar. 7, 1989, disclosed a gripping device for placing electrical or electronic components with terminal pins on a substrate. The gripping device has a pair of grippers movable to one another to close and open their jaws, and a spring-loaded abutment means for pressing the pins of the component into the respective holes on the substrate.

U.S. Pat. No. 4,892,344, issued to Takada et al. on Jan. 9, 1990, disclosed a parallel gripper used for gripping a work for a robot. The gripper has a fluid pressure actuator having two pistons, two transversely slidable fingers, and a power transmission mechanism having two levers each connected between the two pistons and also to one of the fingers.

U.S. Pat. No. 5,236,239, issued to Govang et al. on Aug. 17, 1993, disclosed an adapter for a pick-up device having a plurality of fingers extending from one end of a hollow member, and an apparatus for releasable engagement and transport of an object. The adapter has a first portion for insertion into the hollow member, a stopping portion for limiting the insertion, and a second portion for receiving the object.

U.S. Pat. No. 5,295,723, issued to Kronseder on Mar. 22, 1994, disclosed a gripping bell for bottles. The gripping bell includes a sleeve-like collect chuck having elastic fingers slidably movable by an actuating element for gripping the head of a bottle.

U.S. Pat. No. 5,775,755, issued to Covert et al. on Jul. 7, 1998, disclosed a tube gripper device having a plurality of fingers. The gripper has a cam connected to a solenoid actuator for spreading the fingers apart and a resilient means for returning the fingers.

U.S. Pat. No. 5,948,360 issued to Rao et al. on Sep. 7, 1999, disclosed a modular vial autosampler. The autosampler includes a base unit, a thermal block having a passage way for fluid circulation, a vial rack positioned over the thermal block in heat-conducting relation, and a vial transporter including a main arm projecting from the base unit along a first axis and transportable along a second axis which is perpendicular to the first axis and having a vial gripper assembly mounted on the main arm and transportable along the first axis with a gripper head movable along a third axis perpendicular to both the first axis and second axis.

One of the disadvantages of many conventional vessel picking and placing devices used in conjunction with automated chemical analyzers is that they often have very limited capacities. For example, the prior art devices are often not designed to pick up misaligned vessels. In addition, the prior art devices are often not designed to transfer the vessels in an upright position and mix the contents contained in the vessels in the same cycle. Furthermore, the prior art devices are often not designed with a mechanism to ensure that the vessels are correctly seated before releasing them from the grippers.

Therefore, it is desirable to provide a new method and system for picking and placing vessels which can be used in conjunction with automated chemical instruments and also overcome the disadvantages of conventional methods and systems for handling vessels. Particularly, it is desirable to have methods and systems capable of picking misaligned vessels, and ensuring the vessels are correctly seated before releasing them from the grippers when placing the vessels to avoid jarring or splashing their contents. In addition, it is desirable to have methods and systems capable of transferring the vessels in an upright position and mixing their contents in the same cycle.

SUMMARY OF THE INVENTION

It is an object of the present invention to provide a new method and system for picking and placing vessels used in conjunction with an automated chemical analyzer, such as an immunodiagnostic instrument, with the capacity of picking up misaligned vessels.

It is another object of the present invention to provide a new method and system for picking and placing vessels used in conjunction with an immunodiagnostic instrument, having a mechanism for ensuring the vessels are correctly seated before releasing them from the grippers when placing the vessels, to avoid jarring or splashing the contents of the vessels.

It is a further object of the present invention to provide a new method and system for picking and placing vessels used in conjunction with an immunodiagnostic instrument, which can transfer the vessels in an upright position and mix the contents of the vessels in the same cycle. These and other objects and advantages are achieved in a picking and placing system of the present invention by having a gripper assembly mounted on a positioning mechanism used in conjunction with an automated chemical analyzer, such as an immunodiagnostic instrument. The gripper assembly includes a cylinder having an end rim, and at least two gripping members extending from the end rim of the cylinder in a spaced-apart relationship for receiving therebetween a vessel and holding it by friction. A piston is slidably inserted inside the cylinder, and a plunger is connected to and movable with the piston, and extending between the gripping members for engaging the vessel.

When the vessel is picked up by the gripping members, the plunger will be pushed up by the vessel and, in turn, push the piston up. The gripping members are sufficiently flexible and therefore slightly deflected as the vessel is inserted therebetween and are holding the vessel by friction when the vessel is being transferred. The piston is actuated by an actuator, such as a pneumatic actuator, to push down the plunger for releasing the vessel from the gripping members.

The objects and advantages of the present invention are also achieved in a new picking and placing method for an assay. The method includes the steps of positioning a gripper assembly at a vessel, picking up the vessel by moving the gripper assembly towards the vessel, such that the vessel is inserted between the gripping members, and pushing the plunger away, while leaving a small clearance to allow slight further insertion of the vessel, transferring the vessel as it is held by the gripping members by friction, placing the vessel into a seating position, seating the vessel by further moving the gripper assembly slightly towards the seating position as allowed by the small clearance to ensure that the vessel is correctly seated, and releasing the vessel by moving the gripper assembly away from the seating position while actuating the piston to push the plunger, which in turn pushes the vessel out of the gripping members. The transferring step may be combined with or replaced by a spinning step for mixing the contents of the vessel.

Such an arrangement has been found to provide a number of advantages. As explained in greater detail below, it has been found that the chamfered lower end of the gripping members can handle misaligned vessels. The flexible and expandable gripping members can hold the vessel with friction without disturbing grabbing or jarring motions of actuated gripper fingers. The gripper assembly can transfer and mix the vessel in the same cycle, and the seating step can ensure the vessel to be correctly seated before pushing it out of the gripper to eliminate jarring the vessel or splashing its content.

The system is well suited for use in conjunction with an automated chemical analyzer, such as, but not limited to, immunodiagnostic instruments for immunoassay.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which:

FIG. 3(a) is a side illustrative diagram showing the positioning step of the picking and placing method of the present invention;

FIG. 3(b) is a side illustrative diagram showing the gripping step of the picking and placing method of the present invention;

FIG. 3(c) is a side illustrative diagram showing the transferring step of the picking and placing method of the present invention;

FIG. 3(d) is a side illustrative diagram showing the placing step of the picking and placing method of the present invention;

FIG. 3(e) is a side illustrative diagram showing the seating step of the picking and placing method of the present invention;

FIG. 3(f) is a side illustrative diagram showing the releasing step of the picking and placing method of the present invention.

DETAILED DESCRIPTION OF THE INVENTION

The present invention is directed to a new method and system for picking and placing vessels used in conjunction with an automated chemical analyzer.

Figure 1:
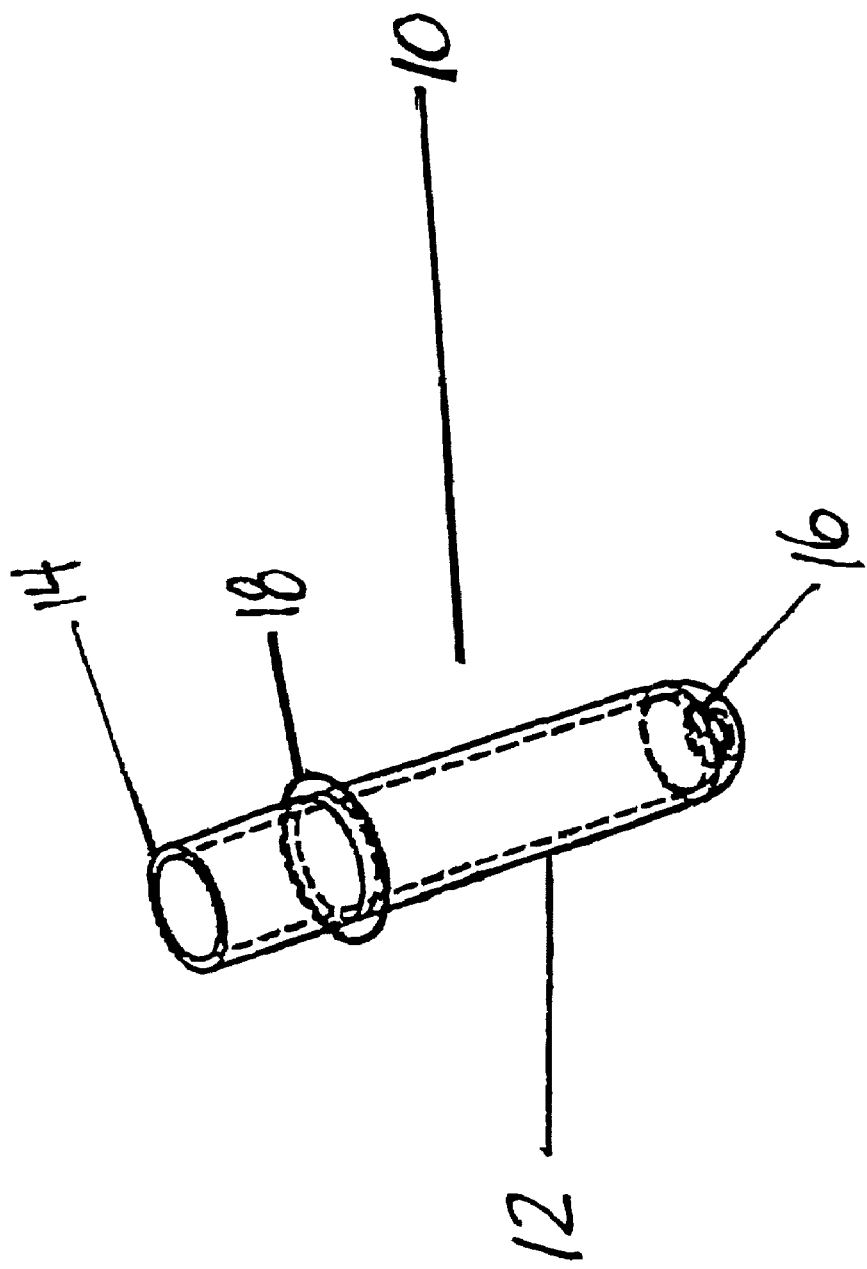
FIG. 1 is a perspective view of a typical vessel for processing and analyzing by an immunodiagnostic instrument.

The picking and placing system of the present invention is a gripper for gripping vessels. A typical vessel 10 is shown in FIG. 1. The vessel 10 has an elongated hollow cylindrical body 12 with an open top end 14 and a closed bottom end 16. On the exterior sidewall of the cylindrical body 12, optionally, there may be a circular flange 18 located below, but adjacent to, the top end 14.

Figure 2:
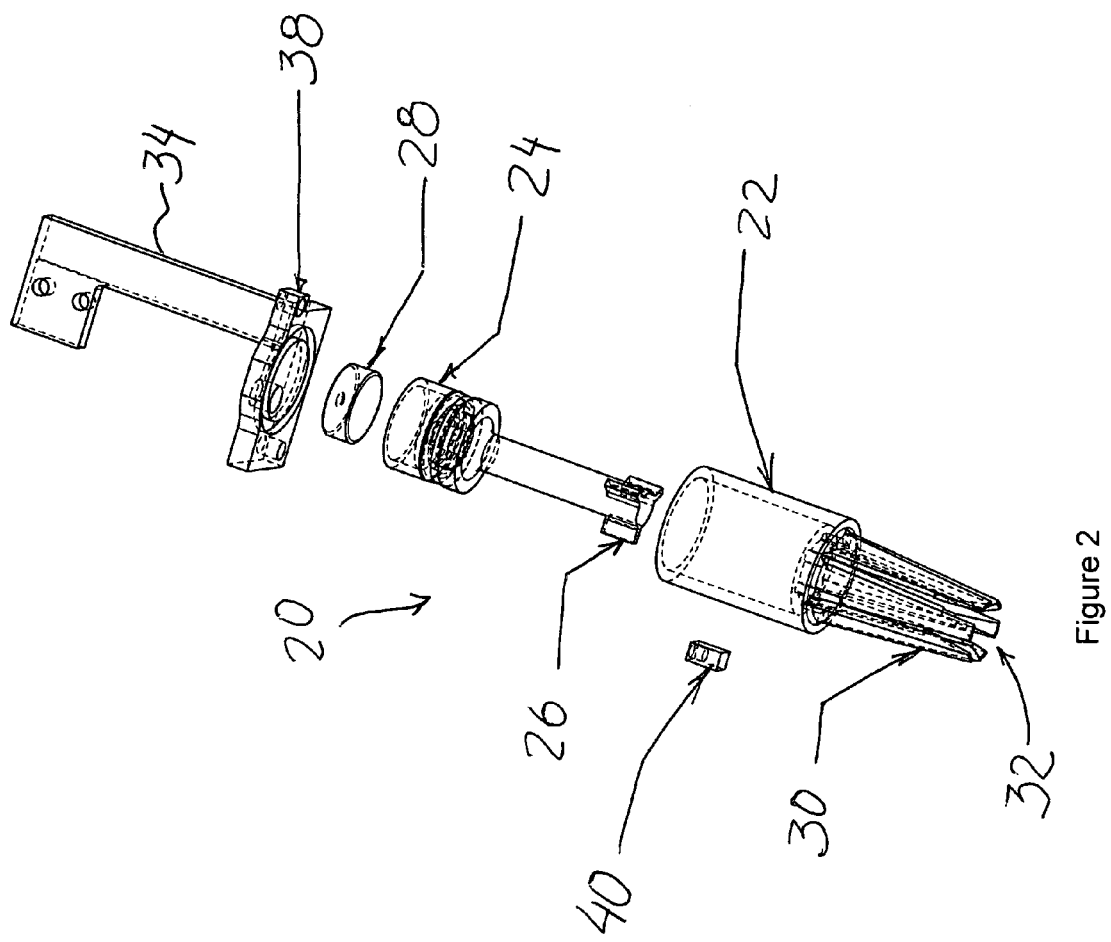
FIG. 2 is an exploded perspective view of a preferred embodiment of a picking and placing gripper of the present invention.

Referring to FIG. 2, there is shown a preferred embodiment of the picking and placing system of the present invention. The picking and placing system includes a gripper assembly 20 mounted on a positioning mechanism (not shown) provided by any known automated chemical analyzer. The gripper assembly 20 has an elongated cylinder 22, a piston 24, an elongated plunger 26, a magnet 28, and multiple gripping members 30. The piston 24 is slideably inserted inside the cylinder 22. The plunger 26 is connected to and travels with the piston 24. The magnet 28 is also mounted to the piston 24.

The gripping members 30 are spring-like or have spring-like properties, so that they are flexible enough to allow them to deform or deflect to allow a vessel to be inserted therebetween yet rigid enough to have adequate strength and tension to hold the vessel, and with spring memories which not only creates sufficient friction between the gripper members 30 and the vessel to hold it in place but also returns them to their original configuration after the vessel is released. The gripping members 30 may be made of semi-rigid flexible material or other suitable materials as long as the materials have the above described properties. Examples of such a material include, but are not limited to, plastic materials and the like.

In one embodiment of the present invention a gripper assembly has at least two gripping members. Both members may be flexible or at least one is flexible and another one is fixed.

Each gripping member 30 has an elongated body with a top end connected to the bottom end of the cylinder 22 and a chamfered free bottom end. The gripping members 30 are connected to the cylinder 22 in a spaced-apart relationship, such that their bottom ends form a slotted expandable circular opening 32 for receiving a vessel. The chamfered bottom ends of the flexible gripping members 30 allow the gripper assembly 20 to pick up misaligned vessels.

The gripper assembly 20 is attached to the positioning mechanism (not shown) by an adapter 34. A bottom circular clamp 38 encloses the cylinder 22 to form a pneumatic actuator, although the actuator may also be actuated by electrical or hydraulics.

When a vessel is picked up by gripper members 30, the plunger 26 pushes the piston 24 up. When a vessel is to be placed down, pressurized air is applied to the piston 24 to push the plunger down, which in turn pushes the vessel out of the gripping members 30. The movement of the piston can be detected by a sensor 40, which can detect the magnetic field of magnet 28. The sensor may be mounted on the exterior sidewall of the cylinder 22 or on the bottom circular clamp 38 of the adapter. This magnet-sensor combination provides a means of verifying whether a vessel has been picked up or placed down. While a magnet sensor is described in this embodiment, it is understood that other possible types of sensors may also be utilized. Examples of such a sensor include, but are not limited to, inductive, capacitive and optical sensors.

Referring to FIGS. 3(a) through 3(f), the method for picking and placing vessels of the present invention include the following basic steps:

1. The positioning step: the gripper assembly 20 is positioned right above a vessel 10 by the positioning mechanism (not shown). Both plunger 26 and piston 24 are in their down positions, and the magnet 28 is not in line with the sensor (not shown);

2. The picking step: the gripper assembly 20 is lowered onto the vessel 10 by a specified distance for insertion of the vessel 10 into the gripping members 30. However, the vessel 10 is not inserted in a maximum possible distance, as a small gap is still left between the lowermost tips of the gripping members 30 and the circular flange 18 of the vessel 10. As the bottom of the plunger 26 contacts the top of the vessel 10, plunger 26 is pushed up to its up position, which in turn pushes the piston 24 to its up position. This places the magnet 28 in the range of the sensor to indicate that the vessel 10 has been picked up by the gripper assembly 20.

3. The transferring step: the gripper assembly 20 is moved by the positioning mechanism to lift the vessel 10 out of the vessel holder (not shown) and transfer the vessel 10 to a position right above a new desired location. This step may be combined with or substituted by a spinning step for mixing the contents of the vessel.

4. The placing step: the gripper assembly 20 is lowered by the positioning mechanism to place the vessel 10 into its new location. The vessel may be placed at a new location or seating or back to the original location or seating.

5. The seating step: at this point, due to tolerance variation or positioning error, the vessel 10 may not be seated correctly in the new location. To ensure that the vessel 10 is correctly seated, the gripper assembly 20 is lowered further by a short distance, which is yet far enough to account for any possible gap between the bottom of the vessel 10 and the bottom of a vessel seating at the new location. If there is no such gap or the gap is filled up during the short lowering movement of gripper assembly 20, the vessel 10 is simply inserted a little further into the gripping members 30 which is allowed by the small gap left between the lowermost tips of the gripping members 30 and the circular flange 18 of the vessel 10. This feature ensures that the vessel 10 is correctly seated down before it is ejected by the gripper assembly 20, thereby preventing any possible jarring of the vessel 10 or splashing of its content.

6. The releasing step: once the vessel 10 is correctly seated, pressurized air is supplied to the cylinder 22 of the gripper assembly. Although pressurized air is supplied to the cylinder 22, the piston 24 does not move down as the vessel which is bottomed out on its seating area and stops the piston from moving down. To release the vessel in the seating area, the positioning mechanism lifts the gripper assembly 20 up, while the compressed air pushes the piston 24 down, which in turn pushes the plunger 26, which in turn leaves the vessel 10 behind as the positioning mechanism is lifted up. When the vessel 10 leaves the gripping members 30, both the plunger 26 and the piston 24 are at their down position again and the sensor no longer detects the presence of the magnet 28, providing the function of verifying that the vessel 10 has been successfully placed. If the sensor did not detect the presence of the vessel after pressurization but before the grippers was lifted, the system would decide that a vessel is not present and had been lost in transfer. At this point the pick and place cycle for this vessel is completed and the gripper assembly is ready to repeat the whole cycle for another vessel.

Figure 4:
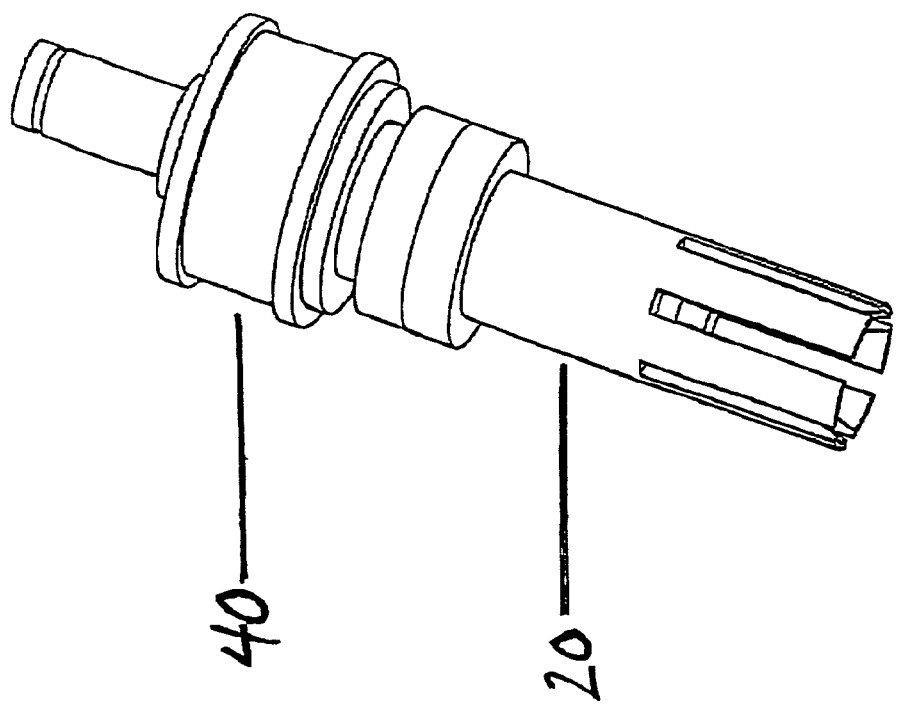
FIG. 4 is a perspective view of an alternative embodiment of a picking and placing gripper of the present invention.

Referring to FIG. 4, in an alternative embodiment of the present invention, the gripper assembly 20 is attached to a spinning mechanism 40. During the transferring step of the cycle, the vessel 10 is spun while held by the gripping members 30 for mixing the content of the vessel 10. Once the desired mixing is accomplished, the vessel is placed to a new location. Alternatively, there is only spinning without transferring, and the vessel is placed back to its original location. As an example, the spin mechanism 40 may include bearings and a pulley attached to the top of the gripper assembly 20, where the pulley may be rotated by a belt or similar device.

The present invention is directed to a vessel pick and place gripper used for providing a smooth transfer of vessels from one module to another without disturbing the contents contained in the vessels. The gripper assembly of the present invention includes the advantageous feature of the chamfered lower end of the gripping members to handle misaligned vessels, the advantageous feature of the flexible and expandable gripping members to hold the vessel with friction and without disturbing grabbing or jarring motions of actuated gripper fingers, the advantageous feature of transferring or mixing the vessel in an upright position, the advantageous feature of ensuring the vessel to be correctly seated before pushing it out of the gripper to eliminate jarring the vessel or splashing its content, and the advantageous feature of combining various tasks, such as positioning and mixing in a same cycle.

The foregoing is meant to illustrate, but not to limit, the scope of the invention. Indeed, those of ordinary skill in the art can readily envision and produce further embodiments, based on the teachings herein, without undue experimentation.

It is to be understood that the forms of the system and the steps of the method depicted in FIGS. 1 through 4 has been chosen only for the purpose of describing particular embodiments and functions of the invention, and that the arrangement of the invention can be addressed in various ways and incorporated in other types of devices and procedures, all of which will be evident to those working in the art.

It is to be understood that the particular arrangement or operation of the gripper assembly of the present invention may vary depending on the automated chemical analyzer it is incorporated or working together with, but that the determination of necessary variation is well within the skill in the art in view of the instant disclosure.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A gripper assembly for picking and placing vessels, comprising:
   a. a cylinder having an end rim;
   b. at least two gripping members, extending from said end rim of said cylinder in a spaced-apart relationship for receiving therebetween a vessel, wherein said gripping members have a spring-like property that allows their deflection as said vessel is inserted therebetween and allows them to hold said vessel by friction;
   c. a piston slidably inserted inside said cylinder; and
   d. a plunger connected to and movable with said piston, the plunger extending between said gripping members for engaging said vessel, wherein the plunger and the gripping members move independently from each other.

2. The gripper assembly of claim 1, further comprising an adapter for mounting said gripper assembly to a positioning mechanism.

3. The gripper assembly of claim 1, wherein at least one of said gripping members is made of semi-rigid flexible material.

4. The gripper assembly of claim 3, wherein said material is plastic material.

5. The gripper assembly of claim 1, wherein said gripping members each have a chamfered bottom end for receiving a misaligned vessel.

6. The gripper assembly of claim 1, further comprising pneumatic means for actuating said piston to push said plunger for releasing said vessel from said gripping members.

7. The gripper assembly of claim 6, wherein said pneumatic means actuates said piston by supplying pressurized air into said cylinder.

8. The gripper assembly of claim 1, further comprising means for detecting whether said vessel has been picked up.

9. The gripper assembly of claim 8, wherein said detecting means comprises a magnet mounted to and movable with said piston, and a sensor fixedly mounted on said cylinder for sensing magnetic field of the magnet.

10. The gripper assembly of claim 8, further comprising an adapter for mounting said gripper assembly to a positioning mechanism, wherein said detecting means comprises a magnet mounted to and movable with said piston, and a sensor fixedly mounted on the adapter.

11. The gripper assembly of claim 8, wherein said detecting means is selected from a group consisting of inductive, capacitive and optical sensors.

12. The gripper assembly of claim 1, further comprising means for mixing the contents of said vessel while it is held by said gripping members.

13. The gripper assembly of claim 12, wherein said mixing means comprises a spin mechanism for spinning said gripper assembly.

14. A method of picking and placing vessels, comprising the steps of:
   a. positioning a gripper assembly at a vessel, the gripper assembly including at least two gripping members extending from a cylinder in a spaced-apart relationship, a piston slidably inserted inside the cylinder, and a plunger connected to the piston, extending between the gripping members and capable of moving independently therefrom;
   b. picking up said vessel by moving said gripper assembly towards said vessel, wherein said gripping members deflect as said vessel is inserted therebetween and wherein said vessel pushes said plunger away; and
   c. transferring said vessel as it is held by said gripping members by friction.

15. The method of claim 14, further comprising the step of mounting said gripper assembly to a positioning mechanism for controlling the movement of said gripper assembly.

16. The method of claim 14, wherein said gripping members each has a chamfered bottom end for receiving a misaligned vessel.

17. The method of claim 14, further comprising the step of spinning said gripper assembly to mix the content of said vessel while said vessel is transferred.

18. The method of claim 14, wherein, during step b, a clearance is left between the gripper assembly and the vessel to allow further insertion of said vessel between said gripping members.

19. The method of claim 18 further comprising steps of:
   d. placing said vessel into a seating;
   e. seating said vessel by further moving said gripper assembly slightly towards said seating as allowed by said clearance to ensure that said vessel is correctly seated; and
   f. releasing said vessel by moving said gripper assembly away from said seating.

20. The method of claim 19, wherein the seating step (e) further comprises actuating said piston to seat said plunger against said vessel.

21. The method of claim 20, further comprising the step of supplying pressurized air to said cylinder to actuate said piston.

22. The method of claim 19, wherein the releasing step (f) further comprises holding the vessel in its seating position with said plunger while moving said gripper away from the vessel.

23. The method of claim 22, wherein the plunger remains seated against said vessel until said gripping members completely disengage said vessel.

24. The method of claim 19, further comprising the step of re-positioning said gripper assembly over a new location before placing said vessel into said seating.

25. The method of claim 19, further comprising the step of positioning said gripper assembly over the same location before placing said vessel into said seating.

26. The method of claim 19, further comprising the step of moving said seating to a new location before placing said vessel into said seating.

27. The method of claim 19, further comprising the step of indexing said seating to a new location before placing said vessel into said seating.

* * * * *